US006528644B1

(12) United States Patent
Wang et al.

(10) Patent No.: US 6,528,644 B1
(45) Date of Patent: Mar. 4, 2003

(54) ACETOACETYLATED SACCHARIDES AND PROCESS OF MAKING THE SAME

(75) Inventors: Peng George Wang, Troy, MI (US); Wenhua Xie, Westland, MI (US); Lei Qiao, Downington, PA (US); Robert G. Nickol, Hockessin, DE (US); Huai N. Cheng, Wilmington, DE (US)

(73) Assignee: Hercules Incorporated, Wilmington, DE (US)

( * ) Notice: Subject to any disclaimer, the term of this patent is extended or adjusted under 35 U.S.C. 154(b) by 0 days.

(21) Appl. No.: 09/963,191

(22) Filed: Sep. 26, 2001

(51) Int. Cl.$^7$ .......................... C07H 1/00; C07H 13/04; C08B 31/02; C08B 37/00; C08B 3/06
(52) U.S. Cl. ................. 536/124; 536/1.11; 536/4.1; 536/123.1; 536/102; 536/107; 536/69; 435/74; 435/101
(58) Field of Search .................. 536/4.1, 124, 1.11, 536/123.1, 102, 107, 69; 435/74, 101

(56) References Cited

U.S. PATENT DOCUMENTS

| | | | |
|---|---|---|---|
| 2,500,029 A | 3/1950 | Hagemeyer | 18/54 |
| 2,521,897 A | 9/1950 | Caldwell | 260/225 |
| 2,627,477 A | 2/1953 | Downey | 106/170 |
| 3,342,806 A | 9/1967 | Ray-Chaudhuri | 260/233.5 |
| 3,361,585 A | 1/1968 | Armour et al. | 106/210 |
| 3,931,069 A | 1/1976 | Lundin | 260/17 R |
| 4,708,821 A | 11/1987 | Shimokawa et al. | 512/12 |
| 5,292,877 A | 3/1994 | Edgar et al. | 536/63 |
| 5,360,843 A | 11/1994 | Edgar et al. | 524/41 |
| 5,565,037 A | 10/1996 | Sobotta et al. | 127/42 |
| 5,770,726 A | 6/1998 | Kuo et al. | 536/69 |

FOREIGN PATENT DOCUMENTS

| | | |
|---|---|---|
| DE | 43 29 293 | 3/1995 |
| WO | 93/03063 | 2/1993 |
| WO | 99/61479 | 12/1999 |
| WO | WO 01/85800 A2 * | 11/2001 |

OTHER PUBLICATIONS

Morrison & Boyd, Organic Chemistry 4$^{th}$ Edition, Allyn and Bacon Inc., Massachusetts, p33–34. 1983.
K. Faber, S. Riva, Synthesis, Oct. 1992, 895–910.
G.E. Jeromin, V. Welsch, Tetrahedron Lett., 1995, vol. 36, No. 37, 6663–64.
K. Suginaka, Y. Hayashi, Y. Yamamoto, Tetrahedron: Assymetry, 1996, vol. 7, No. 4, 1153–58.
U.S. patent application Ser. No. 09/564,575, Cheng et al., filed May 5, 2000.
U.S. patent application Ser. No. 09/791,450, Qiao et al., filed Feb. 23, 2001.

* cited by examiner

*Primary Examiner*—Samuel Barts
*Assistant Examiner*—Michael C. Henry
(74) *Attorney, Agent, or Firm*—Joanne Mary Fobare Rossi

(57) ABSTRACT

A product of acetoacetylated saccharide and the process of making such a product. The process is enzymatic where an enzyme is used as a catalyst for the reaction. The enzymatic process provides better yields and milder process conditions compared to other chemical synthesis process without any enzyme.

27 Claims, No Drawings

ACETOACETYLATED SACCHARIDES AND PROCESS OF MAKING THE SAME

BACKGROUND OF THE INVENTION

1. Field of the Invention

The present invention relates to the acetoacetylation of saccharides with diketene using enzymatic methods.

2. Description of Background and Related Art

Saccharides, both modified and unmodified, are used widely as additives to paper, paints, construction materials, and personal care products. In many applications, it is desirable to modify the chemical structure of a saccharide in order to have additional functionalities. For instance, when a saccharide is acetoacetylated by grafting a bidentate ligating group onto the saccharide, the acetoacetylated saccharide can form complexes with metal ions, such as $Ca^{2+}$, $Fe^{3+}$, and $Al^{3+}$ and therefore remove metal ions from another medium.

Acetoacetylated saccharides have been synthesized using chemical methods. For instance, U.S. Pat. No. 4,708,821 to Shimokawa discloses a chemical method to synthesize acetoacetylated hydroxyethylcellulose (HEC). U.S. Pat. No. 5,360,843 to Edgar et al. discloses a chemical method to synthesize cellulose acetoacetates by contacting a cellulose material with diketene in a solvent system comprising lithium chloride and a carboxamide. U.S. Patent No. 5,565,037 to Sobotta et al. discloses a chemical reaction of glucose with diketene to prepare 1,2,5,6-diacetone-D-glucose. U.S. Pat. Nos. 3,361,585 and 3,342,806 disclose chemical methods of preparing starch-acetoacetalate.

U.S. Pat. application No. 09/564,575, filed May 5, 2000, discloses a process of making an esterified saccharide product using enzymes as a catalyst. It discloses that the reaction between alkyl ketene dimers and saccharides such as cellulosic or guar derivatives to make hydrophobically modified saccharides can be catalyzed by enzymes with high reaction yields. Also, when the chemical synthesis is catalyzed by enzymes, the reaction conditions are much milder than reactions without enzymes.

Enzymes have not been used as catalyst to prepare acetoacetylated saccharides. Therefore, it would be advantageous to use enzymes to catalyze reactions between saccharides and diketene to prepare acetoacetylated saccharides since such enzymatic reactions may have higher yields and lower processing costs due to milder reaction conditions.

SUMMARY OF THE INVENTION

The present invention is a process for producing acetoacetylated saccharides. The process comprising combining saccharide, diketene, and a catalytically effective amount of an enzyme as a reaction mixture under conditions wherein the enzyme catalyzes a reaction between the saccharide and diketene to form the acetoacetylated saccharide. The preferred enzymes are hydrolytic enzymes such as lipases, esterases, and proteases.

BRIEF DESCRIPTION OF THE FIGURE

FIG. 1 illustrates the Brookfield viscosities of 1% solutions of acetoacetylated hydroxyethylcellulose (acetoacetylated HEC) (Sample S), the control solution of sample C of unmodified HEC, and the Brookfield viscosities when 0.25% of $Fe^{3+}$ is added to the acetoacetylated HEC and the control solution.

FIG. 2 illustrates the Brookfield viscosities of acetoacetylated HEC with 0.25% $Fe^{3+}$ (Sample S+Fe) and control solution of unmodified HEC (Sample C) as a function of time.

FIG. 3 illustrates the viscosities of acetoacetylated starch as a function of time and $Ca^{2+}$ concentration and a comparison with metal-ion-free acetoacetylated starch (Control).

DETAILED DESCRIPTION OF THE INVENTION

Unless otherwise stated, all percentages, parts, ratios, etc., are by weight.

Unless otherwise stated, a reference to a compound or component includes the compound or component by itself, as well as in combination with other compounds or components, such as mixtures of compounds.

Further, when an amount, concentration, or other value or parameter, is given as a list of upper preferable values and lower preferable values, this is to be understood as specifically disclosing all ranges formed from any pair of an upper preferred value and a lower preferred value, regardless whether ranges are separately disclosed.

Also as used herein:

The "viscosity" is measured using a DV-I Viscometer (Brookfield Viscosity Lab, Middleboro, Mass.). A selected spindle (number 2) is attached to the instrument, which is set for a speed of 0–80 RPM. A suspension of product in distilled water is heated at 90° C. for 30 min. The resulting mixture is cooled to about 24° C. The Brookfield viscosity spindle is carefully inserted to the solution so as not to trap any air bubbles and then rotated at a speed within the above-mentioned speed range for 3 minutes at 24° C. The units are centipoises.

The term "enzyme deactivating" refers to a process to change the chemical and biochemical nature of the enzyme to eliminate or reduce its activity.

The term "hydrolytic" or "hydrolysis" refers to the cleavage of a bond, such as an ester or an amide bond, which by the addition of water will give two or more products.

The term "degree of substitution" means the average numbers of acetoacetyl group attached to each anhydroglucose unit.

The present invention discloses the synthesis of acetoacetyl derivatives of saccharides using one or more enzymes as reaction catalysts. The synthesis involves reacting diketene with saccharides, which can be either polysaccharides or monosaccharides, or a mixture thereof, in the presence of a catalytically effective amount of an enzyme. During the reaction, the diketene is grafted onto the saccharide to give the acetoacetyl functionality. An example is given below for the reaction between diketene and starch, a polysaccharide. It is expected that the reaction between diketene and other saccharides will have similar chemical structural changes as shown below:

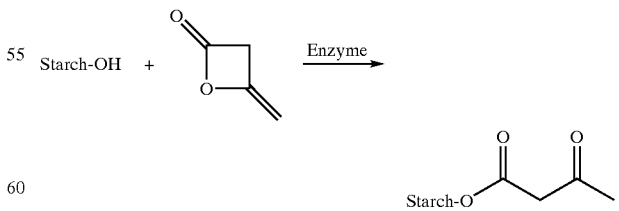

The use of the enzyme speeds up the reaction. The reaction temperature is lower when the enzyme is used in a reaction mixture with a reduction in reaction time as compared to the reaction without using enzyme. Not wishing to be bound by the theory, it is theorized that the enzyme opens the ring of the diketene. The unstable ring-opened diketene group reacts with the hydroxyl groups of the saccharide to form the acetoacetylated saccharide. Thus, the diketene is grafted onto the saccharide to give the acetoacetyl functionality.

The use of enzyme has other benefits. For instance, the use of enzyme in such reaction increases the reaction yield. It is found that, without the use of enzyme as a catalyst, the saccharide/diketene reaction can still proceed but with much lower reaction yield. For instance, in a reaction of glucose, diketene, and a lipase in N,N-dimethylformamide, a glucose-6-acetoacetonate is produced at a yield of about 75%. The same reaction, without the use of enzyme, produces a glucose-6-acetoacetonate at a yield of only about 20%.

A solvent medium can have an impact on the reaction. The enzymatically catalyzed reaction can proceed with or without the presence of a solvent medium, although it is usually preferred to have the reaction proceed in one or more organic solvents. It is found that water and inorganic solvents may reduce the yield and rate of the reaction. Therefore, the reaction is preferably carried out in the absence of or under minimum amount of water or inorganic solvents.

In a typical enzymatic reaction to produce acetoacetylated saccharide in the presence of a solvent, a reaction mixture of saccharide, diketene and enzyme that can catalyze the reaction is combined in one or more organic solvents. The components of this reaction mixture can be added in any particular order. In a preferred method, the catalytic enzyme is added to a mixture that comprises saccharide and diketene. The saccharide can constitute about 0.1 to 95 wt. % of the reaction mixture, the preferred amount is about 0.1 to 15 wt. %, and the most preferred amount is about 3 wt. %. The diketene can constitute about 0.1 to 50 wt. % of the reaction mixture, the preferred amount is about 0.1 to 10 wt. %, and the most preferred amount is about 4 wt. %. The enzyme can constitute about 0.05 to 5 wt. % of the reaction mixture, the preferred amount is about 0.1 to 1 wt. %, and the most preferred enzyme amount is about 0.3 wt. %.

The ratio of diketene to saccharide (ml/g) in a reaction mixture determines whether the acetoacetylated saccharide product will be soluble in water. This in turn determines the application of the acetoacetylated saccharide. In general, when such a ratio is higher, the reaction product is less soluble in water. When the ratio is lower, the reaction product becomes more soluble in water. For instance, when hydroxyethylcelltilose, a polysaccharide, is used as the saccharide, it is found that when such ratio is higher than 0.02, the acetoacetylated saccharide product is insoluble in water. When the ratio is lower than 0.02, the product is progressively soluble in water.

The water-insoluble acetoacetylated saccharides find their applications where different forms of medium are desired. For, instance, the insoluble acetoacetylated saccharide can be used to remove metal ions or other similar chemicals from a liquid, such as aqueous, stream. The soluble acetoacetylated saccharide, however, can be used, for instance, as thickeners and rheology modifiers.

The reaction temperature and time also have impacts on the reaction itself. Generally, the higher the reaction temperature, the less time it takes to reach a targeted product yield of the reaction. The reaction mixture is normally maintained at about 25 to 70° C. for about 1 to 144 hours. The preferred process is to maintain the reaction mixture at about 35 to 65° C, for about 1 to 24 hours. The most preferred process is to maintain the reaction mixture at about 50° C. for about 5 hours.

Depending on different applications of the product, the presence of used catalytic enzyme may or may not present a problem. At the end of the reaction, it is found that enzymes sometimes lose their activities and become deactivated. Enzymes can be deactivated by many factors, such as temperature, organic solvents, metal ions, and other ways known to those skilled in the art. Not wishing to be bound by the theory, it is possible that the enzymes can start to lose some of their activity under the reaction temperature. This loss of activity can progress over the duration of the reaction time. It is possible that by the end of the reaction period, all or most of the activity of the enzyme is lost and therefore, the enzymes are deactivated. The deactivated enzymes become an impurity in the reaction mixture. Although not necessary all the time, in order to ensure that enzymes are deactivated, further enzyme deactivating methods can be used. For instance, the reaction mixture can be further heated to 90–100° C. for about 10 minutes.

Since during the reaction, impurities such as deactivated enzymes and unreacted diketenes and saccharides can be present in the reaction mixture as the reaction progresses and-ends, typical post-reaction purification and separation can be performed to further purify the reaction product. For instance, the reaction product can be extracted with solvents such as dichloromethane. Soxhlet extraction can also be performed with solvents. The product is then dried, under vacuum to constant weight.

The saccharide used in the present invention can be polysaccharide, oligosaccharide, and monosaccharide. The polysaccharide can be, but not limited to, one or more of the following: cellulose, microcrystalline cellulose, hydroxyethylcellulose (HEC), carboxymethylcellulose (CMC), hydroxypropylcellulose (HPC), methylcellulose (MC), ethylcellulose (EC), starch, cationic starch, oxidized starch, pregelatinized starch, modified starch, guar, cationic guar, anionic guar, and modified guar. Preferably, the saccharide comprises hydroxyethylcellulose (HEC) and/or starch. Monosaccharides and oligosaccharides can be used in this invention, including, but not limited to, glucose, lactose, sucrose, maltose, and cellobiose.

The enzyme according to the present invention can comprise one or more enzymes that can catalyze the reaction between the saccharide and diketene. Preferably, the enzyme comprises at least one hydrolytic enzyme. The enzyme can be derived from synthetic or natural sources. The enzyme may be added directly to the reaction mixture as a suspension or may be immobilized on an inert carrier in the reactor. The enzyme may be in fully or in partially active form. The hydrolytic enzyme of the present invention includes, but not limited to, lipase, esterase, protease, or mixtures thereof. Preferably, the enzyme is a lipase, such as Lipase PS from Amano or CLONEZYMES™ ESL-001 series from Diversa.

The presence of a solvent is preferred for this enzymatic reaction. Many different solvents and the mixture thereof can be used as a solvent in the reaction mixture. The preferred solvent is at least one of the polar aprotic solvents. A polar aprotic solvent has a moderately high dielectric constant and does not contain acidic hydrogen (e.g., R. T. Morrison and R. N. Boyd, "Organic Chemistry", $4^{th}$ Ed., p.33). Polar aprotic solvents include but are not limited to N,N-dimethylformamide (DMF), N,N-dimethylacetamide (DMAc), N-methylpyrrolidone (NMP), dimethylsulfoxide (DMSO), tetramethylene sulfone, and pyridine. The preferred solvent is at least one of N,N-dimethylformamide and dimethylsulfoxide.

Although it is preferred to have at least one solvent in the reaction mixture, the synthesis of the present invention can also proceed in the absence of solvents.

In reactions carried out in the absence of solvents, the amounts of saccharide, diketene, and enzyme used to carry out the reaction are different from those when solvent is present. In such a reaction environment, the enzyme can constitute about 0.1 to 10 wt. % of the reaction mixture, the preferred amount is about 0.5 to 8 wt. %, and the most preferred amount is about 5 wt. %. The saccharide can constitute about 0.1 to 95 wt. % of the reaction mixture, the preferred amount is about 40 to 95 wt. %, and the most preferred amount is about 50 to 60 wt. %. The diketene can constitute about 1 to 50 wt. % of the reaction mixture, the preferred amount is about 5 to 25 wt. %, and the most preferred amount is about 10 to 15 wt. %.

One of the useful properties of the product made using the present enzymatic process that its viscosity can be manipulated using additional treatment. Normally, after the enzymatic reaction, the acetoacetylated saccharide samples of the present invention show either no change or a small increase in solution viscosity compared to unmodified saccharide. However, when a metal ion, such as $Ca^{2+}$ or $Fe^{3+}$, is added to the reaction mixture, the viscosity of the product solution increases noticeably. Not wishing to be bound by theory, it is theorized that the metal ion forms a bridge across two or more acetoacetyl groups, or acetoacetyl and saccharide groups, and thereby forms a "crosslink" between two or more polymer chains. The viscosity may increase or decrease with time. For instance, the viscosity increases with time when the metal ion is added to acetoacetylated HEC but decreases with time when the metal ion is added to acetoacetylated starch. The addition of excess metal ions to an acetoacetylated saccharide solution decreases its viscosity. Not wishing to be bound by theory, it is theorized that excess ions tie up all the available acetoacetyl groups and thus decrease the "crosslink" interactions among the different chains of the acetoacetylated saccharide.

Because of the unique properties, the product of the present invention can find many different applications. For instance, since the acetoacetyl groups of the acetoacetylated saccharide can easily form complexes with metal ions, the acetoacetylated saccharide solution can be used to remove metal ions from another medium. By carefully monitoring the weight ratio of diketene and saccharide, a water insoluble acetoacetylated saccharide can be prepared to remove metal ions from a water stream.

Without further elaboration, it is believed that one skilled in the art can, using the preceding description, utilize the present invention to its fullest extent. Moreover, the enzyme-catalyzed process can be carried out on a non-polysaccharide polymer, producing a non-polysaccharide acetoacetylated polymer.

The invention is illustrated by the following Examples, which are provided for the purpose of representation, and are not to be construed as limiting the scope of the invention. Unless stated otherwise, all percentages, parts, etc., are by weight.

EXAMPLE 1

A reaction mixture of glucose (0.36 g from Aldrich), diketene (0.31 g, from Aldrich), and lipase (ESL-001-07 from Diversa, 20 mg) was prepared in 10 ml of anhydrous DMF. The reaction mixture was stirred at room temperature for 5 days. Additional 10 mg of same lipase was added to the reaction mixture on the third day. Thin layer chromatography (TLC) indicated one predominant product, which is isolated using column chromatography. The reaction yield was 75%. $^1$H-NMR shows signals of α,β-glucose and also two single peaks at 2.24 and 3.34 ppm, which are from the acetoacetonate. In the $^{13}$C-NMR spectrum, peaks at 28.7, 49.6, 167.6, and 201.9 ppm belong to acetoacetonate. The peaks at 64.05 and 64.13 ppm are assigned to be C-6 in the α,β-glucose. These two peaks are 3 ppm downfield from the unreacted glucose. This suggests that the acetoacetonate is regiospecifically attached to C-6 in the α,β-glucose.

EXAMPLE 2

A reaction mixture of HEC (0.3 g, Hercules), diketene (0.4 ml, Aldrich), and lipase (20 mg from Diversa,) was prepared in 10 ml of anhydrous DMF The reaction mixture was stirred at room temperature for 5 days. Additional 10 mg of same lipase was added to the reaction mixture on the third day. After reaction, the reaction mixture was poured into an excess amount of diethyl ether (60 ml). The precipitate was separated and extracted with hexane/$CHCl_3$ (2:1 mole ratio) for 24 hours. A solid of 0.343 g was obtained. The analysis using $^1$H-NMR, $^{13}$C-NMR, and IR reveals that the solid product is predominantly HEC-acetoacetonate. The HEC-acetoacetonate thus prepared does not dissolve completely in water. The degree of substitution (D.S.) varies when different lipase is used with different reaction time as summarized in Table 1. Table 1. Impact of enzyme and reaction time on the product's degree of substitution.

TABLE 1

Impact of enzyme and reaction time on the product's degree of substitution.

| Enzyme | Reaction Time (days) | Diketene (ml)/ HEC (g) | D.S. | Solubility in Water |
|---|---|---|---|---|
| ESL-001-02 | 5 | 1.33 | 0.83 | No |
| ESL-001-05 | 5 | 1.33 | 0.68 | No |
| ESL-001-06 | 6 | 1.33 | 0.16 | No |
| ESL-001-07 | 6 | 1.33 | 0.38 | No |

EXAMPLE 3

The solubility of acetoacetylated saccharide product in water depends on the ratio of diketene to saccharide in the reaction mixture at the start of the reaction. A comparison study was conducted. A reaction mixture of HEC (2 g, Hercules) and a different amount of diketene was prepared in an organic solvent of either NMP or DMAc, with or without enzyme. Each reaction was allowed to proceed at room temperature for 5 days. The product was precipitated in acetone and recovered. Table 2 summaries the results. It shows that when the ratio of diketene/HEC (ml/g) is less than 0.02, the acetoacetylated HEC is soluble in water.

TABLE 2

Solubility of acetoacetylated HEC in water

| Expt. | Solvent used | Diketene added (ml) | Diketene (ml)/ HEC (g) | Enzyme used | Solubility in Water |
|---|---|---|---|---|---|
| A1 | NMP | 3 | 1.5 | Yes | No |
| A2 | NMP | 3 | 1.5 | No | No |
| A3 | DMAc | 3 | 1.5 | Yes | No |
| A4 | DMAc | 3 | 1.5 | No | No |
| B1 | NMP | 0.3 | 0.15 | Yes | No |
| B2 | NMP | 0.3 | 0.15 | No | No |

TABLE 2-continued

Solubility of acetoacetylated HEC in water

| Expt. | Solvent used | Diketene added (ml) | Diketene (ml)/ HEC (g) | Enzyme used | Solubility in Water |
|---|---|---|---|---|---|
| B3 | DMAc | 0.3 | 0.15 | Yes | No |
| B4 | DMAc | 0.3 | 0.15 | No | yes |
| C1 | DMAc | 0.3 | 0.15 | No | yes |
| C2 | DMAc | 0.16 | 0.08 | No | yes |
| C3 | DMAc | 0.08 | 0.04 | No | yes |
| C4 | DMAc | 0.04 | 0.02 | No | Yes |
| D1 | DMAc | 0.04 | 0.02 | No | No |
| D2 | DMAc | 0.03 | 0.015 | No | No |
| D3 | DMAc | 0.02 | 0.01 | No | Yes |
| D4 | DMAc | 0.01 | 0.005 | No | Yes |

Lines C4 and D1 under similar conditions gave differing solubility results; it is theorized that the drying conditions may have affected solubility, i.e., one sample may have became more "hornified" or internally cross-linked and the other did not, thereby affecting solubility.

EXAMPLE 4

A reaction mixture with diketene/HEC ratio (ml/g) of 0.01 was prepared in an organic solvent of DMAc without enzyme. The reaction was allowed to proceed at room temperature for 5 days. The product was precipitated in acetone and collected by filtration. The product was then dissolved in water to prepare a 1% solution (Sample S). The solution's Brookfield viscosity was measured at different measuring rpm rates. The results are shown in FIG. 1. A control sample of unmodified HEC at the same solution level (Sample C) was also studied for its viscosity. Another comparison study was also conducted by adding 0.25 wt. % of $Fe^{3+}$ to the solutions of control sample and acetoacetylated HEC solution (Samples C+Fe and S+Fe).

FIG. 1 shows that the viscosities of control solution (Sample C), Sample S, and Sample C+Fe are the same. However, the viscosity for Sample S+Fe is distinctly higher.

Sample S+Fe solution and the control solution, Sample C, were monitored for their viscosities for two days. The viscosity of Sample S+Fe increased with time and the viscosity of Sample C decreased with time (FIG. 2). The pH of both solutions remained at 2 during the experiment.

EXAMPLE 5

Starch (Stalok 140 from Staley, 10 g) was added to DMSO (200 ml) and the mixture was heated to 90–95° C. to give a clear solution. The solution was cooled to 50° C. Diketene (5 ml, Aldrich) was added followed by Lipase PS (from Amano, 0.8 g). The reaction mixture was stirred at 50° C. for 5 h and then poured into isopropyl alcohol (600 ml). The precipitates were collected by vacuum filtration and further purified by Soxhlet extraction with IPA as the solvent for 6 hours. The solid was then dried under vacuum at 50° C. to constant weight and the yield of this experiment was 10.02 g.

Interestingly, the viscosity of acetoacetylated starch increased significantly compared to unmodified starch. The samples were measured at 4% solution. The viscosity of unmodified starch was 8.34 cps and the viscosity of acetoacetylated starch was 66 cps.

EXAMPLE 6

The impact of different metal ions to the viscosity of acetoacetylated starch was also studied. When 0.05% of $Fe^{3+}$ was added to the acetoacetylated starch of Example 5, the viscosity increased to 91.1 cps. When 0.05% of $Ca^{2+}$ was added to the acetoacetylated starch of Example 5, the viscosity increased to 274.2 cps.

The concentration of the metal ion (such as $Ca^{2+}$) also plays a role on the viscosity of the acetoacetylated starch solution. FIG. 3 shows that when the metal concentration increases, the viscosity first increases and then decreases. The addition of $Ca^{2+}$ at 0.05% gives the largest viscosity increase.

EXAMPLE 7

The present invention can be practiced without using of any organic solvent. A reaction mixture of lipase (0.5 g, Amano), diketene (5 ml, Aldrich), and maltodextrin (5 g, Grain Processing Corp.) was prepared without any organic solvent medium. The reaction mixture was heated to 50° C. for 6.5 hours and was precipitated with acetone. The solids were collected using vacuum filtration and further purified by Soxhlet extraction using chloroform. The yield was 3.3 g. IR and $^1$H-NMR confirmed that diketene was grafted onto maltodextrin.

From the foregoing description, one skilled in the art can easily ascertain the essential characteristics of this invention, and without departing from the spirit and scope thereof, can make various changes and modifications of the invention to adapt it to various usages and conditions. For instance, in all examples, the products are dried under vacuum. But the product can also be dried under atmospheric pressure.

What is claimed is:

1. A process of producing acetoacetylated saccharides comprising combining saccharide, diketene, and a catalytically effective amount of an enzyme as a reaction mixture under conditions wherein the enzyme catalyzes a reaction between the saccharide and diketene to form the acetoacetylated saccharide.

2. The process according to claim 1 wherein the enzyme comprises a hydrolytic enzyme.

3. The process according to claim 2 wherein the hydrolytic enzyme comprises at least one of lipases, esterases, and proteases.

4. The process according to claim 3 wherein the hydrolytic enzyme comprises a lipase.

5. The process according to claim 1 wherein the enzyme is present at an amount of about 0.05 wt. % to about 5 wt. % of the reaction mixture, wherein the reaction mixture further comprises a solvent.

6. The process according to claim 5 wherein the enzyme is present at an amount of about 0.1 wt. % to about 1 wt. % of the reaction mixture.

7. The process according to claim 1 wherein the enzyme is present at an amount of about 0.1 wt. % to about 10 wt. % of the reaction mixture, wherein the reaction mixture does not comprise a solvent.

8. The process according to claim 7 wherein the enzyme is present at an amount of about 0.5 wt. % to about 8 wt. % of the reaction mixture.

9. The process according to claim 5 wherein the solvent comprises at least one polar aprotic solvent.

10. The process according to claim 9 wherein the solvent comprises at least one of N,N-dimethylformamide, N,N-dimethylacetamide, N-methylpyrrolidone, dimethylsulfoxide, tetramethylene sulfone, and pyridine.

11. The process according to claim 10 wherein the solvent is at least one of N,N-dimethylformamide and dimethylsulfoxide.

12. The process according to claim 1 further comprising maintaining the temperature of the reaction mixture at about 25 to 70° C. for about 1 to 144 hours.

13. The process according to claim 12 comprising maintaining the temperature of the reaction mixture at about 35 to 65° C. for about 1 to 24 hours.

14. The process according to claim 1 wherein the saccharide comprises at least one of glucose, cellulose, microcrystalline cellulose, hydroxyethylcellulose, carboxymethylcellulose, hydroxypropylcellulose, methylcellulose, ethylcellulose, starch, cationic starch, oxidized starch, pre-gelatinized starch, modified starch, and guar.

15. The process according to claim 14 wherein the saccharide is a hydroxyethylcellulose.

16. The process according to claim 14 wherein the saccharide is a starch.

17. The process according to claim 1 wherein the combining reaction mixture comprises 0.1 to 95 wt. % of the saccharide based on the total weight of the reaction mixture, wherein the reaction mixture further comprises a solvent.

18. The process according to claim 17 wherein the combining reaction mixture comprises 0.1 to 15 wt. % of the saccharide based on the total weight of the reaction mixture.

19. The process according to claim 1 wherein the combining reaction mixture comprises 0.1 to 95 wt. % of the saccharide based on the total weight of the reaction mixture, wherein the reaction mixture does not comprise a solvent.

20. The process according to claim 19 wherein the combining reaction mixture comprises 40 to 95 wt. % of the saccharide based on the total weight of the reaction mixture.

21. The process according to claim 20 wherein the combining reaction mixture comprises 50 to 65 wt. % of the saccharide based on the total weight of the reaction mixture.

22. The process according to claim 1 wherein the combining reaction mixture comprises 0.1 to 50 wt. % of the diketene based on the total weight of the reaction mixture, wherein the reaction mixture fuirther comprises a solvent.

23. The process according to claim 22 wherein the combining reaction mixture comprises 0.1 to 10 wt. % of diketene based on the total weight of the reaction mixture.

24. The process according to claim 1 wherein the combining reaction mixture comprises 1 to 50 wt. % of diketene based on the total weight of the reaction mixture, wherein the reaction mixture does not comprise a solvent.

25. The process according to claim 24 wherein the combining reaction mixture comprises 5 to 25 wt. % of diketene based on the total weight of the reaction mixture.

26. The process according to claim 25 wherein the combining reaction mixture comprises about 10 to 15 wt. % of diketene based on the total weight of the reaction mixture.

27. A process of producing acetoacetylated saccharides comprising combining a saccharide, diketene, and a catalytically effective amount of an enzyme as a reaction mixture under conditions wherein the enzyme catalyzes a reaction between the saccharide and diketene to form the acetoacetylated saccharide;

wherein the enzyme is added to the mixture of a saccharide and diketene to catalyze a reaction between: the saccharide and the diketene;

wherein the enzyme is a lipase and present at an amount of about 0.1 to about 1 wt. % of the reaction mixture;

wherein the saccharide is a hydroxyethylcellulose or starch present at an amount of about 0.1 to about 15 wt. % of the combining reaction mixture;

wherein the diketene is present at an amount of about 0.1 to about 10 wt. % of the combining reaction mixture;

wherein the reaction mixture further comprises a solvent of at least one of N,N-dimethylformamide and dimethylsulfoxide;

wherein the process further comprises maintaining the temperature of the reaction mixture at about 35 to about 65° C. for about 1 to about 24 hours.

* * * * *